US007501511B2

(12) United States Patent
Moinet et al.

(10) Patent No.: US 7,501,511 B2
(45) Date of Patent: Mar. 10, 2009

(54) PROCESS FOR RESOLVING AIMINES THAT ARE USEFUL FOR THE TREATMENT OF DISORDERS ASSOCIATED WITH INSULIN RESISTANCE SYNDROME

(75) Inventors: Gérard Moinet, Orsay (FR); Daniel Cravo, Sartrouville (FR); Thierry Passemar, Breuillet (FR)

(73) Assignee: Merck Patent GmbH, Darmstadt (DE)

( * ) Notice: Subject to any disclaimer, the term of this patent is extended or adjusted under 35 U.S.C. 154(b) by 205 days.

(21) Appl. No.: 10/551,956

(22) PCT Filed: Apr. 6, 2004

(86) PCT No.: PCT/EP2004/002476

§ 371 (c)(1),
(2), (4) Date: Oct. 6, 2005

(87) PCT Pub. No.: WO2004/089917

PCT Pub. Date: Oct. 21, 2004

(65) Prior Publication Data

US 2006/0223803 A1   Oct. 5, 2006

(30) Foreign Application Priority Data

Apr. 10, 2003   (FR) .................................. 03 04486

(51) Int. Cl.
*C07D 251/10* (2006.01)
*A61K 31/53* (2006.01)
*A61P 3/10* (2006.01)

(52) U.S. Cl. ...................... 544/206; 544/208; 544/209; 514/245

(58) Field of Classification Search ................. 544/206, 544/208, 209; 514/245
See application file for complete search history.

(56) References Cited

U.S. PATENT DOCUMENTS 3,894,027 A   7/1975   Sohar et al.
2003/0109530 A1   6/2003   Brodt et al.

FOREIGN PATENT DOCUMENTS

JP   54014986   2/1979
WO   WO 0155122   8/2001

OTHER PUBLICATIONS

Jacques J et al: "Enantiomers Racemates, and Resolutions, Passage" Enantiomers, Racemates, and Resolutions, Malabar, Krieger, US, 1991, pp. 256,259-260, XP002027010.

*Primary Examiner*—Venkataraman Balasubramanian
(74) *Attorney, Agent, or Firm*—Millen, White, Zelano, Branigan, P.C.

(57) ABSTRACT

The present invention is directed towards a process for resolving a racemic amino compound derived from dihydro-1,3,5-triazines. The invention is also directed towards the enantiomers of amino derivatives of dihydro-1,3,5-triazines and to their use for the preparation of medicaments, in particular for the treatment of diabetes and malaria.

22 Claims, 2 Drawing Sheets

Figure 1:
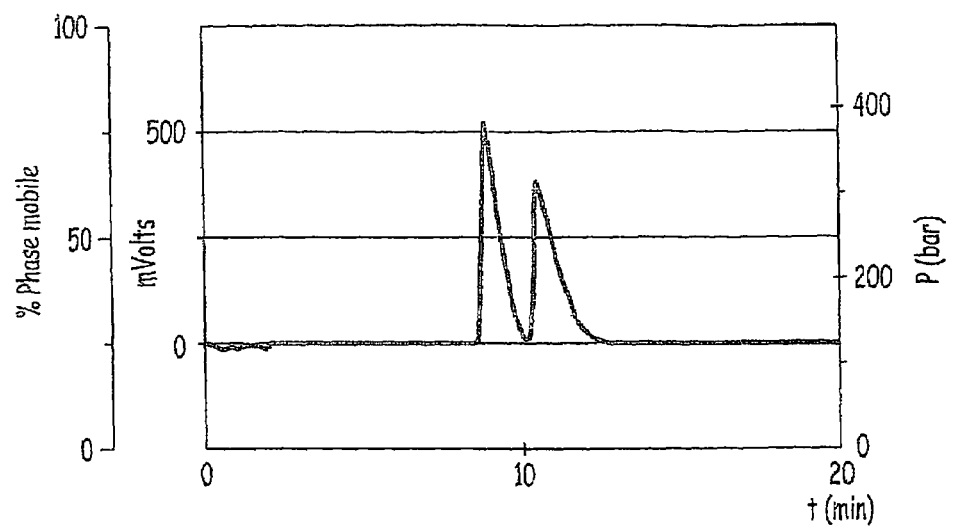

PROCESS FOR RESOLVING AIMINES THAT ARE USEFUL FOR THE TREATMENT OF DISORDERS ASSOCIATED WITH INSULIN RESISTANCE SYNDROME

The present invention is directed towards a process for resolving amines derived from dihydro-1,3,5-triazines from the corresponding racemic mixture.

Compounds of the dihydrotriazine family are advantageous especially on account of their pharmacological properties.

There are numerous documents in the literature concerning dihydro-1,3,5-triazines. Thus, patent application WO 01/53276 describes dihydrotriazines having the following formula:

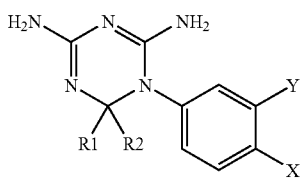

in which R1 may be hydrogen, as trihydrofolate reductase inhibitors, especially having antimalarial activity.

Abstract JP 48064088 describes dihydrotriazines having the following formula:

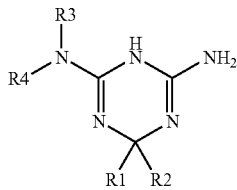

in which R1 may be hydrogen. These compounds are described as having activity in reducing the level of glucose in the blood.

Abstract JP 54014986 describes dihydrotriazines having the following formula:

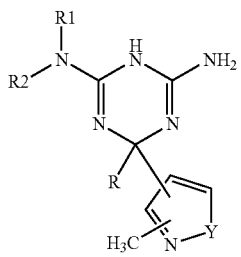

in which R may be hydrogen, as compounds with antidiabetic activity.

U.S. Pat. No. 3,287,366 describes dihydrotriazines of the formula

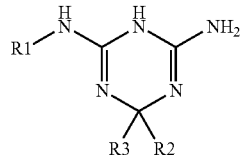

in which R3 may be hydrogen, as herbicidal compounds.

Patent application WO 01/55122 describes dihydrotriazines according to the following formula:

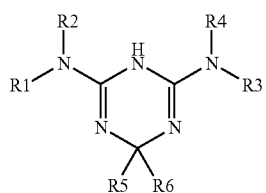

in which R5 may be hydrogen. These compounds can be used in the treatment of disorders associated with insulin resistance syndrome.

These compounds all bear an asymmetric carbon when the R groups specified above represent hydrogen. The corresponding enantiomers have not been published. Similarly, none of the documents published to date describes or suggests a method for the preparation of them.

It is known that the biological activity of enantiomers of racemic compounds can differ considerably depending on the two enantiomers. Consequently, there is often one enantiomer that has more pronounced activity, making it more advantageous as an active principle in a medicament.

The use of this enantiomer instead of the racemate is advantageous. Specifically, the higher activity of the identified enantiomer makes it possible to reduce the dosage of active principle in the medicament. The lower dosage then allows a reduction of the adverse side effects. It is thus desirable for an active principle to be composed of only the pure enantiomer that has the largest desired biological effects.

Numerous methods exist for separating a racemic mixture into its two pure enantiomers. For further information in this respect, reference is made especially to the book "Chirotechnology" by R. A. Sheldon (1993) published by Dekker.

Examples of such processes that may be mentioned include:

- separation based on a physical property difference
- separation based on the use of biotechnological methods (whole cells, enzymes, etc.)
- separation based on the use of chromatographic methods
- separation based on the formation of diastereoisomers (salts, addition of a chiral centre).

The aim of the present invention is thus to propose a separation of a racemic mixture of amino derivatives of dihydro-1,3,5-triazines as defined above.

During a separation of a racemic mixture, it is necessary to have available a method for monitoring the enantiomeric excess. The standard method consists in monitoring the change in the optical rotation of the diastereoisomeric salt or of the enantiomer. However, this method is relatively unsuitable in the case of compounds with a low optical rotation.

The use of chiral HPLC is also a solution frequently used. However, it has been found that this method does not make it possible to obtain an exploitable result.

We have discovered, unexpectedly, that the use of chiral HPLC in supercritical phase allowed us to visualize the two enantiomers. This technology has recently undergone major developments in the analytical and preparative fields. The fundamental principles of this technology are described, for example, in the book "Chromatographies en phase liquide et supercritique [Liquid-phase and supercritical-phase chromatography]" published by Masson, Paris, 1991.

The process according to the invention thus allows easy and economical access to the pure enantiomers.

The separation process more particularly involves a step of asymmetric conversion of a racemic compound of structure (I) below:

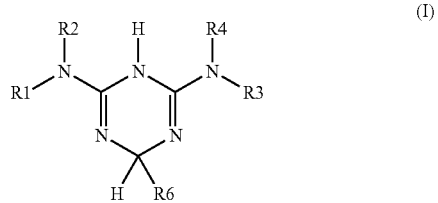

in which:

R1, R2, R3 and R4 are chosen independently from the following groups:
H;
alkyl (C1-C20) optionally substituted by halogen, alkyl (C1-C5), alkoxy (C1-C5) or cycloalkyl (C3-C8);
alkylene (C2-C20) optionally substituted by halogen, alkyl (C1-C5) or alkoxy (C1-C5);
alkyne (C2-C20) optionally substituted by halogen, alkyl (C1-C5) or alkoxy (C1-C5);
cycloalkyl (C3-C8) optionally substituted by alkyl (C1-C5) or alkoxy (C1-C5);
heterocycloallyl (C3-C8) bearing one or more hetero atoms chosen from N, O and S and optionally substituted by alkyl (C1-C5) or alkoxy (C1-C5);
aryl (C6-C14) alkyl (C1-C20) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl or carboxyethyl;
aryl (C6-C14) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl or carboxyethyl; or
heteroaryl (C1-C13) bearing one or more hetero atoms chosen from N, O and S and optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl or carboxyethyl;
R1 and R2, on the one hand, and R3 and R4, on the other hand, possibly forming with the nitrogen atom an n-membered ring (n between 3 and 8) optionally comprising one or more hetero atoms chosen from N, O and S and possibly being substituted by one of the following groups: amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl or carboxyethyl;

R6 is chosen from the following groups:
alkyl (C1-C20) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl or carboxyethyl;
alkylene (C2-C20) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl or carboxyethyl;
alkyne (C2-C20) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl or carboxyethyl;
cycloalkyl (C3-C8) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl or carboxyethyl;
heterocycloalkyl (C3-C8) bearing one or more hetero atoms chosen from N, O and S and optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl or carboxyethyl;
aryl (C6-C14) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl or carboxyethyl;
heteroaryl (C1-C13) bearing one or more hetero atoms chosen from N, O and S and optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl or carboxyethyl;
aryl (C6-C14) alkyl(C1-C5) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl or carboxyethyl.

For one preferred subgroup of compounds of the formula (I), R3 and R4 represent a hydrogen atom. For another preferred subgroup of compounds of the formula (I), R1 and R2 represent a C1 to C3 alkyl group, advantageously methyl.

The compounds of the formula (I) that are particularly preferred are:
(+)-2-amino-3,6-dihydro-4-dimethylamino-6-methyl-1,3,5-triazine hydrochloride;
(−)-2-amino-3,6-dihydro-4-dimethylamino-6-methyl-1,3,5-triazine hydrochloride;
(+)-2-amino-6-cyclohexyl-3,6-dihydro-4-dimethylamino-1,3,5-triazine hydrochloride; and
(−)-2-amino-6-cyclohexyl-3,6-dihydro-4-dimethylamino-1,3,5-triazine hydrochloride.

The process according to the invention more generally includes the following steps:
the preparation of diastereoisomeric salts of the compounds according to formula (I);

the purification of the diastereoisomer obtained; and the release of the pure enantiomer from the purified diastereoisomer.

The resolution is performed in the presence of a chiral reagent.

Since the compounds targeted are amines, a chiral acid is advantageously used as chiral reagent for the resolution of the racemic mixture.

The diastereoisomeric salt thus obtained is then subjected to a purification step, and the enantiomer is then released from the purified salt.

Examples of chiral acids that can be used include: (+)-D-di-O-benzoyltartaric acid, (−)-L-di-O-benzoyltartaric acid, (−)-di-O,O'-p-tolyl-L-tartaric acid, (+)-di-O,O'-p-tolyl-D-tartaric acid, R(+)-malic acid, S-(−)-malic acid, (+)-camphanic acid, (−)-camphanic acid, R(−)-1,1'-binaphthalene-2,2'-diyl hydrogen phosphate, S(+)-1,1'-binaphthalene-2,2'-diyl hydrogen phosphate, (+)-camphoric acid, (−)-camphoric acid, S(+)-2-phenylpropionic acid, R(−)-2-phenylpropionic acid, D(−)-mandelic acid, L(+)-mandelic acid, D-tartaric acid, L-tartaric acid, or a mixture thereof.

The chiral acid is preferably chosen from the group consisting of (−)-di-O,O'-p-tolyl-L-tartaric acid, (+)-di-O,O'-p-tolyl-D-tartaric acid, R(−)-1,1'-binaphthalene-2,2'-diyl hydrogen phosphate, S(+)-1,1'-binaphthalene-2,2'-diyl hydrogen phosphate, D-tartaric acid and L-tartaric acid.

The formation of the diastereoisomeric salt may be performed in a polar solvent or a solvent mixture comprising at least one polar solvent.

The formation of the diastereoisomeric salt may be performed at a temperature ranging from −10° C. to the reflux point of the solvent or solvent mixture.

One is the diastereoisomeric salt has been isolated, and more generally at any moment, the enantiomeric excess is checked by means of supercritical chiral HPLC.

In the supercritical-phase HPLC technique, the mobile phase percolated through the stationary phase contains a gas in supercritical state.

This gas is preferably carbon dioxide, on account of its low cost and its high volatility, and also its harmlessness in the atmosphere. Thus, this technique has, especially in industrial plants in which the amounts of mobile-phase mixture may be large, the advantage of being harmless both to the workers and to the environment. Also, its high volatility allows an easy separation of the purified compound once the purification is complete.

The HPLC mobile phase will thus generally comprise 60% to 100% by volume of $CO_2$. The remainder is prepared using a solvent or a mixture of solvents. They are preferably polar solvents used as modifiers of the polarity of the mobile phase. These solvents may be chosen, for example, from alcohols, halogenated alkyls, ethers and nitriles.

The HPLC mobile phase may also comprise acidic or basic polarity modifiers. Examples of acidic polarity modifiers that may especially be mentioned include optionally halogenated carboxylic acids, such as trifluoroacetic acid, acetic acid and formic acid. Basic polarity modifiers that may be mentioned include alkylamines, such as diethylamine and triethylamine. The HPLC mobile phase generally comprises from 0.01% to 2% by volume of acidic or basic polarity modifier.

The HPLC stationary phase (column) is chosen from enantioselective stationary phases. Columns based on oligosaccharides or polysaccharides are especially suitable. Such columns are commercially available, especially under the name Chiralcel® from Daicel or Chirose® from Chiralsep.

The temperature and pressure in the column are adjusted such that the gas contained in the mobile phase is in supercritical state. A pressure of from 80 to 350 bar, preferably from 100 to 200 bar and most particularly from 120 to 170 bar, is generally selected.

The temperature is preferably adjusted to a value of from 30 to 50° C.

The diastereoisomeric salt in solution is injected in an amount that depends on the columns used, and especially on their size. The process will especially be performed with volumes of between 5 and 50 µl.

The flow rate of the mobile phase is generally adjusted to 1 to 3.5 ml/minute and preferably 2 to 3 ml/minute.

Once the diastereoisomeric salt has been isolated, it is purified to the desired diastereoisomeric purity, for example by recrystallizing in a suitable solvent or solvent mixture.

The purified diastereoisomeric salt is then dissociated in basic or acidic medium in a suitable solvent or solvent mixture. Thus, a desired enantiomer is recovered from the racemic mixture of the compound of structure (I).

If the enantiomer derived from the racemic mixture of structure (I) is isolated in base form, it may be salified using a pharmaceutically acceptable organic or mineral acid.

A subject of the invention is also the enantiomers of the formula (I) in which R1, R2, R3, R4 and R6 have the meaning given above.

The enantiomers are particularly useful for the preparation of medicaments for the treatment of diabetes, disorders associated with insulin resistance syndrome or alternatively diabetes-related pathologies, such as atherosclerosis and micro- and macroangiopathy. Finally, the enantiomers of the invention are also useful for the preparation of medicaments that are useful for the treatment of malaria.

Figure 2:
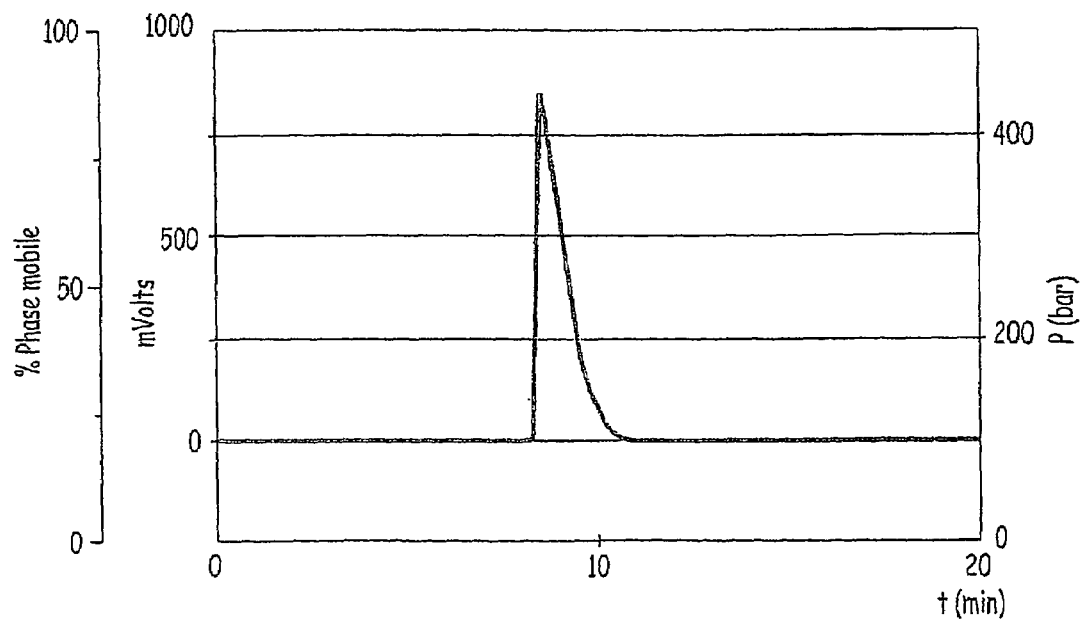
Figure 3:
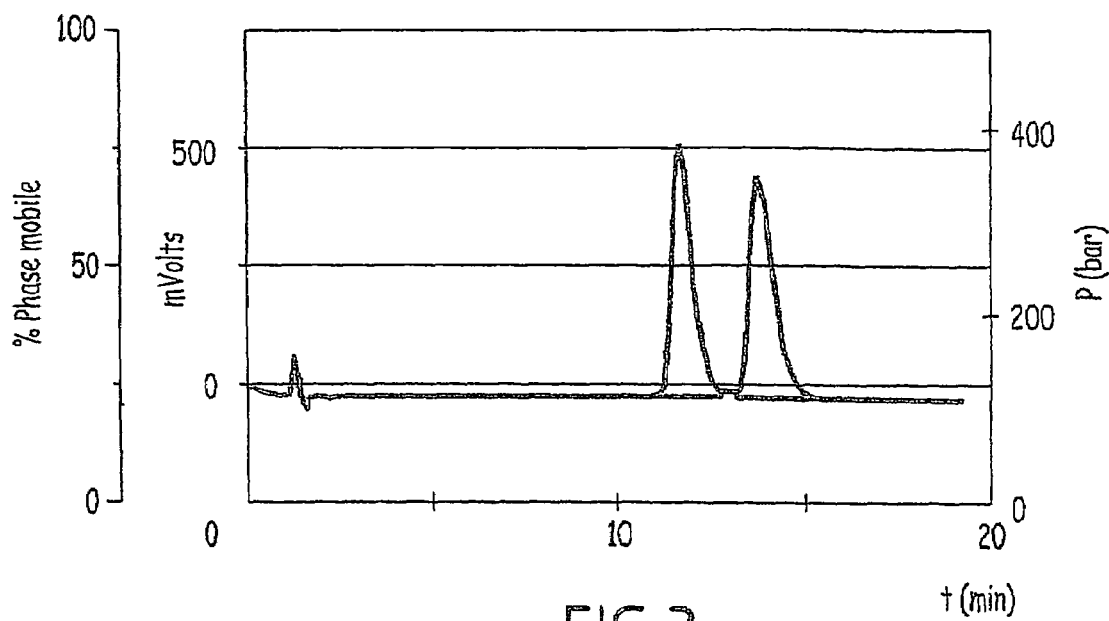
Figure 4:
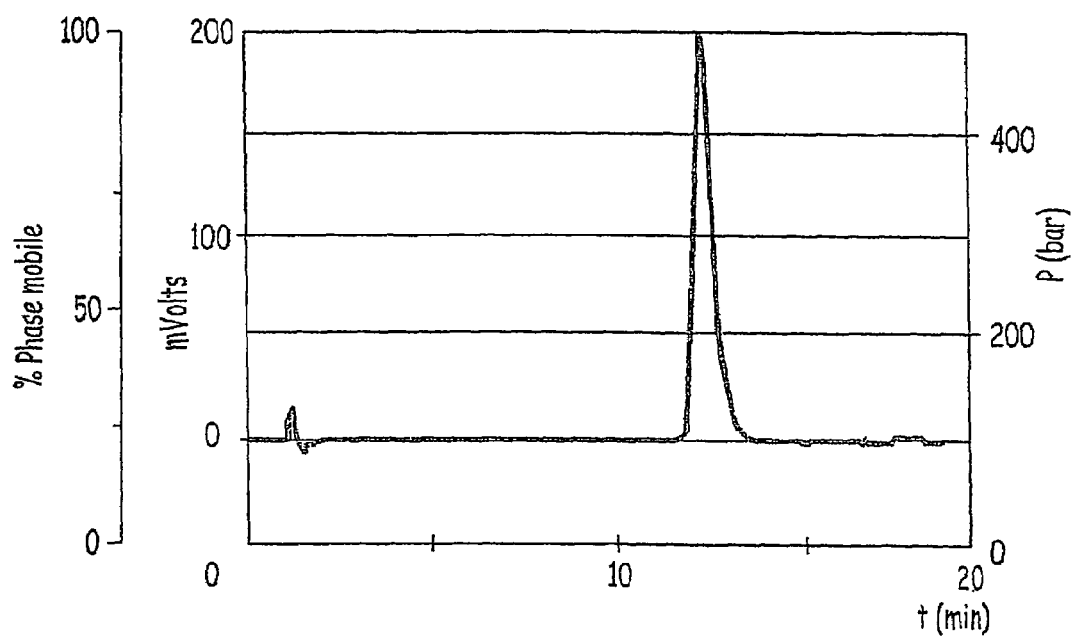

The invention is illustrated with the aid of the following figures, which show:

FIG. 1: supercritical-phase chiral HPLC chromatogram of the starting racemic compound of Example 1, the retention time being 8.77 minutes for the (+) enantiomer and 10.48 minutes for the (−) enantiomer;

FIG. 2: supercritical-phase chiral HPLC chromatogram of the (+) enantiomeric compound of Example 1 after purification;

FIG. 3: supercritical-phase chiral HPLC chromatogram of the starting racemic compound of Example 2, the retention time being 11.74 minutes for the (+) enantiomer and 13.84 minutes for the (−) enantiomer;

FIG. 4: supercritical-phase chiral HPLC chromatogram of the (−) enantiomeric compound of Example 2 after purification.

The invention will also be described in further detail with the aid of the examples that follow, which are given in a non-limiting manner.

EXAMPLE 1

Preparation of (+)-2-amino-3,6-dihydro-4-dimethylamino-6-methyl-1,3,5-triazine hydrochloride A solution of 348.5 g of (−)-di-O,O'-p-tolyl-L-tartaric acid in 1 L of methanol is added to a solution of 200 g of (±)-2-amino-3,6-dihydro-4-dimethylamino-6-methyl-1,3,5-triazine (chromatogram of FIG. 1) in 1 L of methanol. After stirring for 5 hours, the precipitate formed is filtered off by suction (33% yield, 70% ee determined by supercritical chiral HPLC performed on an SF3 model "supercritical fluid chromatography system" from Gilson, under the following conditions:

pressure: 150 bar flow rate: 2.5 ml/minute stationary phase: Chirose® W1-T (available from Chiralsep)

mobile phase: 69.8% $CO_2$, 30% methanol and 0.2% diethylamine column temperature: 40° C.

UV detection at 240 nm injection volume: 20 µl concentration: 1 mg/ml

The composition of the mobile phase is indicated in terms of volume under the operating conditions of the column.

The diastereoisomeric salt is recrystallized from a DMF/ 95° ethanol mixture (1/1) (38% yield; 94% ee).

The enriched salt is suspended in a water/ethyl acetate mixture (1/1) and the whole is cooled to 0° C. One equivalent of 2M hydrochloric acid is added such that the temperature does not exceed 5° C.

Vigorous stirring is maintained for 15 hours. The organic phase is recovered in order to recycle the (−)-di-O,O'-p-tolyl-L-tartaric acid. The aqueous phase is concentrated. The solid obtained is recrystallized from 95° ethanol to give 20 g of a white powder (>99% ee; overall yield 10%, $\alpha_D^{26°\ C.}$ (C=5, $H_2O$)=+2.10) (FIG. 2).

EXAMPLE 2

Preparation of (−)-2-amino-6-cyclohexyl-3,6-dihydro-4-dimethylamino-1,3,5-triazine hydrochloride A solution of 150 g of (±)-2-amino-6-cyclohexyl-3,6-dihydro-4-dimethylamino-1,3,5-triazine (FIG. 3) in 1.5 l of ethyl acetate and 750 ml of 95° ethanol is maintained at 80° C. until dissolution is complete. A solution of 100.9 g of D(−)-tartaric acid in 750 ml of 95° ethanol is added, heating is maintained for one hour and the mixture is then left to cool to room temperature. The precipitate formed is filtered off by suction (30% yield, 80.6% ee determined by supercritical chiral HPLC on an SF3 model "supercritical fluid chromatography system" from Gilson, under the following conditions:

pressure: 150 bar flow rate: 2.5 ml/minute stationary phase: Chiralcel® DO (available from Daicel)

mobile phase: 91% $CO_2$, 8% methanol and 1% diethylamine column temperature: 40° C.

UV detection at 240 nm injection volume: 20 µl concentration: 1 mg/ml

The composition of the mobile phase is given in terms of volume under the operating conditions of the column.

The solid is dissolved in water and isobutanol is added. Sodium hydroxide is added with vigorous stirring and, after a few minutes, the organic phase is isolated, dried over sodium sulfate and concentrated. The concentrate is taken up in acetonitrile and cooled to 0° C., and one equivalent of hydrogen chloride dissolved in isopropanol is added such that the temperature does not exceed 5° C. After a few hours, the precipitate formed is filtered off by suction and then recrystallized from ethanol (24 g; >99% ee; overall yield 16%, $\alpha_D^{24°\ C.}$ (C=5, $H_2O$)=−109.40) (FIG. 4).

The invention claimed is:

1. A process for resolving a racemic compound of the formula (I):

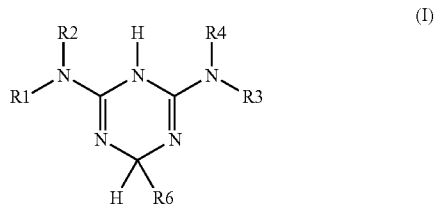

in which:

R1, R2, R3 and R4 are chosen independently from the following groups:

H;

alkyl (C1-C20) optionally substituted by halogen, alkyl (C1-C5) or alkoxy (C1-C5), or cycloalkyl (C3-C8);

alkylene (C2-C20) optionally substituted by halogen, alkyl (C1-C5), or alkoxy (C1-C5);

alkyne (C2-C20) optionally substituted by halogen, alkyl (C1-C5), or alkoxy (C1-C5);

cycloalkyl (C3-C8) optionally substituted by alkyl (C1-C5) or alkoxy (C1-C5);

heterocycloalkyl (C3-C8) bearing one or more hetero atoms chosen from N, O and S and optionally substituted by alkyl (C1-C5) or alkoxy (C1-C5);

aryl (C6-C14) alkyl (C1-C20) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl, or carboxyethyl;

aryl (C6-C14) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl, or carboxyethyl; or heteroaryl (C1-C13) bearing one or more hetero atoms chosen from N, O and S and optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl, or carboxyethyl; or R1 and R2, on the one hand, and R3 and R4, on the other hand, can also form with the nitrogen atom a 3 to 8-membered ring optionally comprising one or more hetero atoms chosen from N, O and S and possibly being substituted by one or more of the following groups: amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl or carboxyethyl;

R6 is chosen from the following groups:

alkyl (C1-C20) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl, or carboxyethyl;

alkylene (C2-C20) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl, or carboxyethyl;

alkyne (C2-C20) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl or carboxyethyl;

cycloalkyl (C3-C8) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl, or carboxyethyl;

heterocycloalkyl (C3-C8) bearing one or more hetero atoms chosen from N, O and S and optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl, or carboxyethyl;

aryl (C6-C14) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl, or carboxyethyl; or heteroaryl (C1-C13) bearing one or more hetero atoms chosen from N, O and S and optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl or carboxyethyl; or aryl (C6-C14) alkyl (C1-C5) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl, or carboxyethyl;

comprising:

a) reacting the racemic compound of formula (I) with a chiral acid, selected from (−)-di -O, O'-p-tolyl-L-tartaric acid, R(−)-1,1'-binaphthalene-2,2'-diyl hydrogen phosphate, and S(+)-1,1'-binaphthalene-2,2'-diyl hydrogen phosphate, to form a corresponding diastereoisomeric salt;

b) purifying the diastereoisomeric salt thus obtained; and c) releasing the diastereoisomeric salt as one of the two enantiomers of the formula (I) in the form of a pharmaceutically acceptable salt.

2. A process according to claim 1, wherein R1 and R2 are each $CH_3$.

3. A process according to claim 1, wherein R3 and R4 are each H.

4. A process according to claim 1, further comprising checking the enantiomeric excess by means of supercritical chiral HPLC.

5. A process according to claim 4, wherein the HPLC mobile phase comprises 60% to 100% by volume of $CO_2$.

6. A process according to claim 4, wherein the HPLC mobile phase also comprises a polar solvent.

7. A process according to claim 4, wherein the HPLC mobile phase also comprises an acidic or basic polarity modifier.

8. A process according to claim 4, wherein the HPLC stationary phase is based on oligosaccharides or polysaccharides.

9. A process according to claim 1, wherein the enantiomer is released from the diastereoisomeric salt by dissociating the diastereoisomeric salt in basic or acidic medium in a suitable solvent or solvent mixture.

10. A process according to claim 1, wherein said one of the two enantiomers of the formula (I) is:
   (+)-2-amino-3,6-dihydro-4-dimethylamino-6-methyl-1,3,5-triazine hydrochloride;
   (−)-2-amino-3,6-dihydro-4-dimethylamino-6-methyl-1,3,5-triazine hydrochloride;
   (+)-2-amino-6-cyclohexyl-3,6-dihydro-4-dimethylamino-1,3,5-triazine hydrochloride; or
   (−)-2-amino-6-cyclohexyl-3,6-dihydro-4-dimethylamino-1,3,5-triazine hydrochloride.

11. A process according to claim 1, wherein R1 and R2 are each $C_1$-$C_3$ alkyl.

12. A process according to claim 2, wherein R3 and R4 are each H.

13. A process according to claim 11, wherein R3 and R4 are each H.

14. A process according to claim 13, wherein R6 is alkyl (C1-C20) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, nifluoromethyl, carboxyl, carboxymethyl, or carboxyethyl.

15. A process according to claim 13, wherein R6 is cycloalkyl (C3-C8) optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (Cl -C5), cyano, trifluoromethyl, carboxyl, carboxymethyl, or carboxyethyl.

16. A process according to claim 13, wherein R6 is heterocycloalkyl (C3-C8) bearing one or more hetero atoms chosen from N, O and S and optionally substituted by amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxyl, carboxymethyl, or carboxyethyl.

17. A process according to claim 13, wherein R6 is aryl (C6-C14) optionally substituted by amino, hydroxyl, thio, halogen, alkyl (C1-C5), alkoxy (C1-C5), alkyithia (C1-C5), alkylamino (C1-C5), aryl (C6-C14) oxy, aryl (C6-C14) alkoxy (C1-C5), cyano, trifluoromethyl, carboxyl, carboxymethyl, or carboxyethyl.

18. A process according to claim 13, wherein R6 is heteroaryl (C1-C13) bearing one or more hetero atoms chosen from N, O and S and optionally substituted be amino, hydroxyl, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluromethyl, carboxyl, carboxymethyl or carboxyethyl.

19. A process according to claim 13, wherein R6 is aryl (C6-C14) alkyl(C1-C5) optionally substituted by amino, hydroxyl, thio, halogen, alkyl (C1-C5), alkoxy (C1-C5), alkylthio (C1-C5), alkylamino (C1-C5), aryl (C6-C14), oxy, aryl (C6-C14), alkoxy (C1-C5), cyano, trifluoromethyl, carboxyl, carboxymethyl, or carboxyethyl.

20. A process according to claim 14, wherein R6 is alkyl (C1-C20).

21. A process according to claim 15, wherein R6 is cycloalkyl (C3-C8).

22. A process according to claim 1, wherein said pharmaceutically acceptable salt is a hydrochloride salt.

* * * * *

UNITED STATES PATENT AND TRADEMARK OFFICE
CERTIFICATE OF CORRECTION

| | | |
|---|---|---|
| PATENT NO. | : 7,501,511 B2 | Page 1 of 1 |
| APPLICATION NO. | : 10/551956 | |
| DATED | : March 10, 2009 | |
| INVENTOR(S) | : Gerard Moinet | |

It is certified that error appears in the above-identified patent and that said Letters Patent is hereby corrected as shown below:

On the Title page, Title: line 1, reads "AIMINES" should read -- AMINES --
Column 10, line 23, claim 10 reads "wherein, R3" should read -- wherein R3 --
Column 10, line 34, claim 14 reads "nifluoromethyl," should read -- trifluoromethyl, --
Column 10, line 51, claim 17 reads "alkyithia" should read -- alkylthio --
Column 10, line 57, claim 17 reads "substituted be amino," should read -- substituted by amino, --
Column 10, line 60, claim 18 reads "trifluromethyl," should read -- trifluoromethyl, --
Column 10, line 65, claim 19 reads "aryl (C6-C14), oxy," should read -- aryl (C6-C14) oxy, --
Column 10, line 66, claim 19 reads "aryl (C6-C14), alkoxy" should read -- aryl (C6-C14) alkoxy --

Signed and Sealed this

Twenty-ninth Day of September, 2009

David J. Kappos
*Director of the United States Patent and Trademark Office*